United States Patent
Hirai et al.

(10) Patent No.: US 9,582,875 B2
(45) Date of Patent: Feb. 28, 2017

(54) DEFECT ANALYSIS ASSISTANCE DEVICE, PROGRAM EXECUTED BY DEFECT ANALYSIS ASSISTANCE DEVICE, AND DEFECT ANALYSIS SYSTEM

(71) Applicant: HITACHI HIGH-TECHNOLOGIES CORPORATION, Tokyo (JP)

(72) Inventors: Takehiro Hirai, Tokyo (JP); Ryo Nakagaki, Tokyo (JP); Kenji Obara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/400,341

(22) PCT Filed: Apr. 1, 2013

(86) PCT No.: PCT/JP2013/059813
§ 371 (c)(1),
(2) Date: Nov. 11, 2014

(87) PCT Pub. No.: WO2013/168487
PCT Pub. Date: Nov. 14, 2013

(65) Prior Publication Data
US 2015/0139531 A1  May 21, 2015

(30) Foreign Application Priority Data

May 11, 2012  (JP) .................................. 2012-109052

(51) Int. Cl.
*G06K 9/00* (2006.01)
*G06T 7/00* (2006.01)
(Continued)

(52) U.S. Cl.
CPC .......... *G06T 7/001* (2013.01); *G01N 21/9501* (2013.01); *G01N 21/95607* (2013.01);
(Continued)

(58) Field of Classification Search
CPC .......... G06T 7/001; G06T 2207/30148; G01N 23/2251; G01N 21/9501
(Continued)

(56) References Cited

U.S. PATENT DOCUMENTS

2007/0023653 A1  2/2007  Toyoda et al.
2009/0180680 A1*  7/2009  Satou ...................... G06T 7/001
                                                      382/144
(Continued)

FOREIGN PATENT DOCUMENTS

JP  2009-010286 A  1/2009
JP  2010-028136 A  2/2010
(Continued)

*Primary Examiner* — Ruiping Li
(74) *Attorney, Agent, or Firm* — Miles & Stockbridge P.C.

(57) ABSTRACT

Conventionally, there was no method for automatically selecting the layers to be overlaid, so when the number of layers to be overlaid was large, there was a problem that much time was required for selecting the layers. It is an object of the present invention to provide a defect image analysis method capable of specifying patterns and layers in which a defect occurs by overlaying defect images to be analysis targets and design layout data, and a defect image analysis system capable of improving the efficiency to select the layers from the design layout data. The present invention is characterized in dividing analysis target images for each hierarchy corresponding to a manufacturing process and generating a plurality of layers; calculating a degree of matching between each of the layer division images and each design layer of the design layout data; and specifying a design layer with a highest degree of matching of the each design layer as a design layer corresponding to the layer division image.

12 Claims, 10 Drawing Sheets

Figure 1:
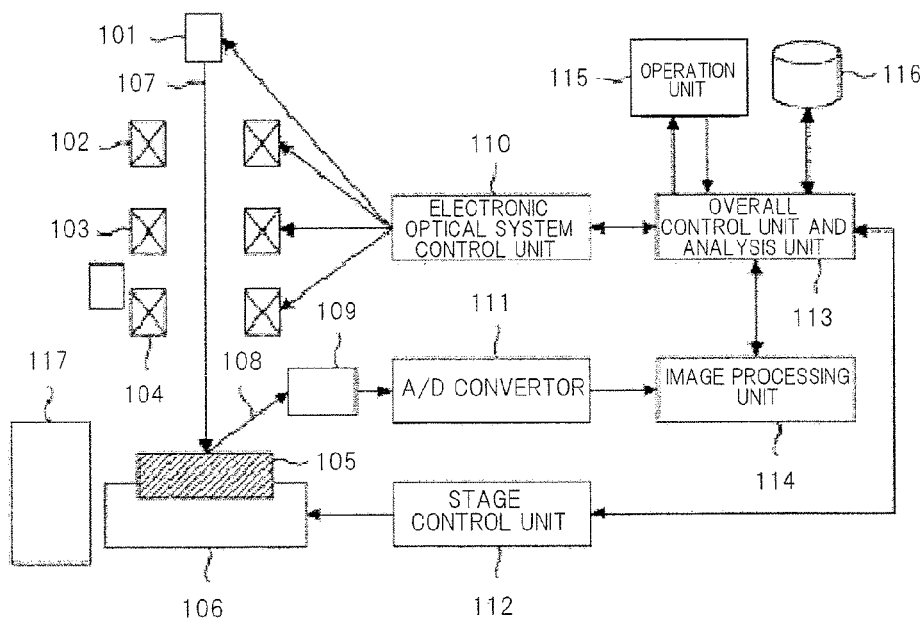

(51) Int. Cl.
*H01L 21/66* (2006.01)
*G01N 21/95* (2006.01)
*G01N 23/225* (2006.01)
*G01N 21/956* (2006.01)

(52) U.S. Cl.
CPC ....... *G01N 23/2251* (2013.01); *G06T 7/0006* (2013.01); *H01L 22/12* (2013.01); *G01N 2223/6116* (2013.01); *G01N 2223/646* (2013.01); *G06T 2207/10061* (2013.01); *G06T 2207/30148* (2013.01)

(58) Field of Classification Search
USPC ........................................................ 382/149
See application file for complete search history.

(56) References Cited

U.S. PATENT DOCUMENTS

| | | |
|---|---|---|
| 2012/0098952 A1 | 4/2012 | Nakahira et al. |
| 2012/0131529 A1 | 5/2012 | Hayakawa et al. |

FOREIGN PATENT DOCUMENTS

| | | |
|---|---|---|
| WO | WO 2011/004534 A1 | 1/2011 |
| WO | WO 2011/039908 A1 | 4/2011 |

\* cited by examiner

FIG. 4
(a) DEFECT OBSERVATION IMAGE
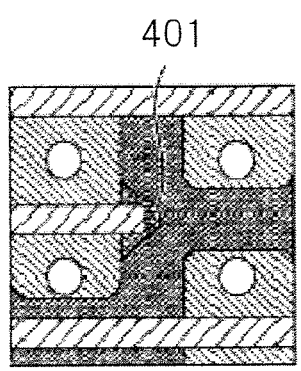
401
(b) DESIGN DATA
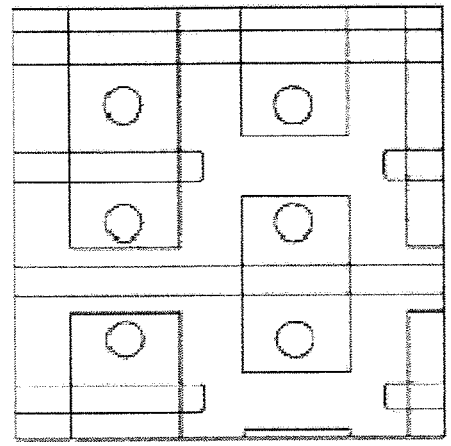
(c) OVERLAY OF DEFECT OBSERVATION IMAGE AND DESIGN DATA
402
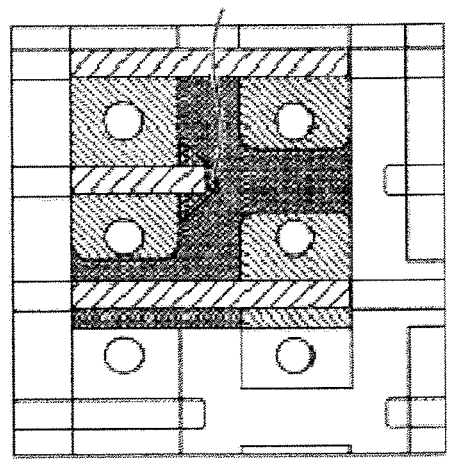

FIG. 5
(a) WHEN DEFECT REGION IS SMALL WITH RESPECT TO FOV
501
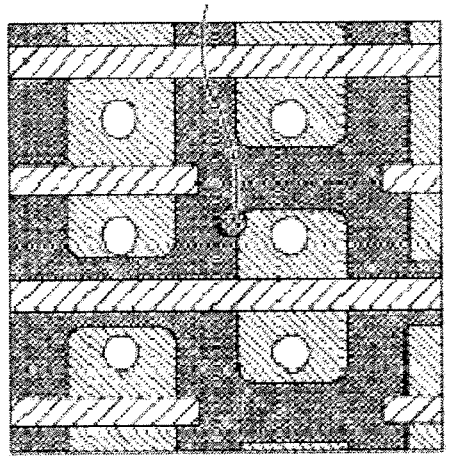
(b) WHEN DEFECT REGION IS LARGE WITH RESPECT TO FOV
502
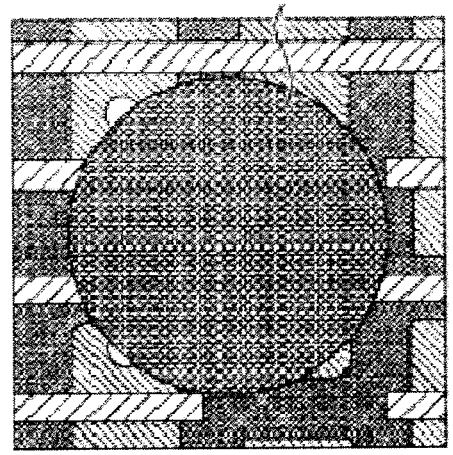

FIG. 7
(a) IN CASE OF ONE LAYER
THRESHOLD VALUE 1
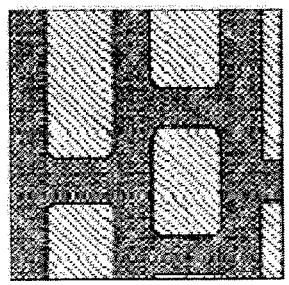
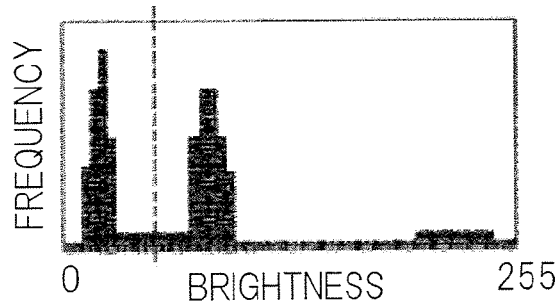
(b) IN CASE OF TWO LAYERS
THRESHOLD   THRESHOLD
VALUE 1     VALUE 2
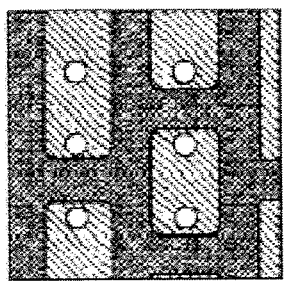
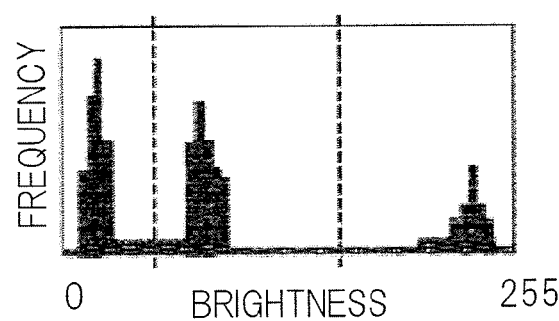
(c) IN CASE OF THREE LAYERS
THRESHOLD THRESHOLD THRESHOLD
VALUE 1    VALUE 2    VALUE 3
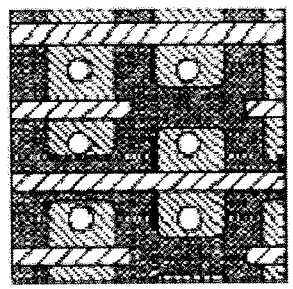
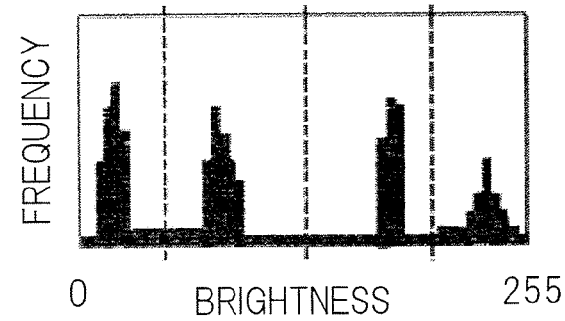

FIG. 8
(a)
OBSERVATION IMAGE
BEFORE LAYER
DIVISION PROCESSING
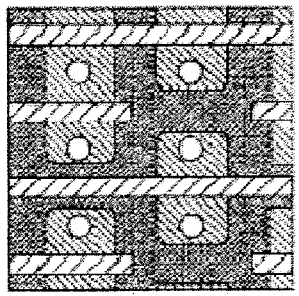
(b1)
LAYER 1 AFTER LAYER
DIVISION PROCESSING
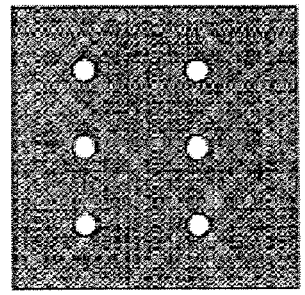
(c1)
DESIGN LAYER 1 AS
MATCHING TARGET
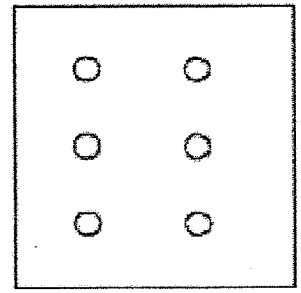
(b2)
LAYER 2 AFTER LAYER
DIVISION PROCESSING
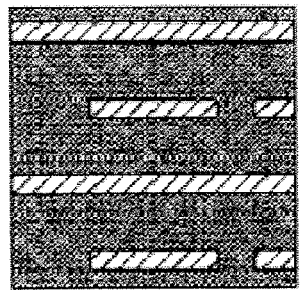
(c2)
DESIGN LAYER 2 AS
MATCHING TARGET
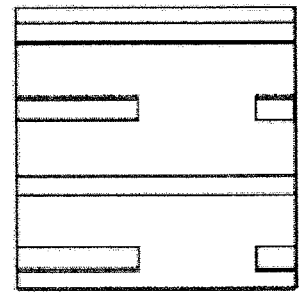
(b3)
LAYER 3 AFTER LAYER
DIVISION PROCESSING
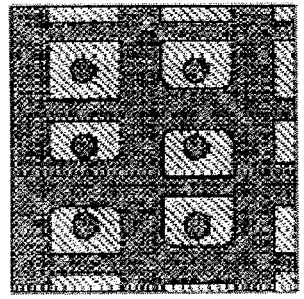
(c3)
DESIGN LAYER 3 AS
MATCHING TARGET
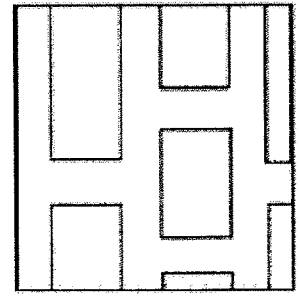

FIG. 9
(a) RESULT THAT LAYER 1 IS ARRANGED IN ORDER OF PATTERN DENSITY
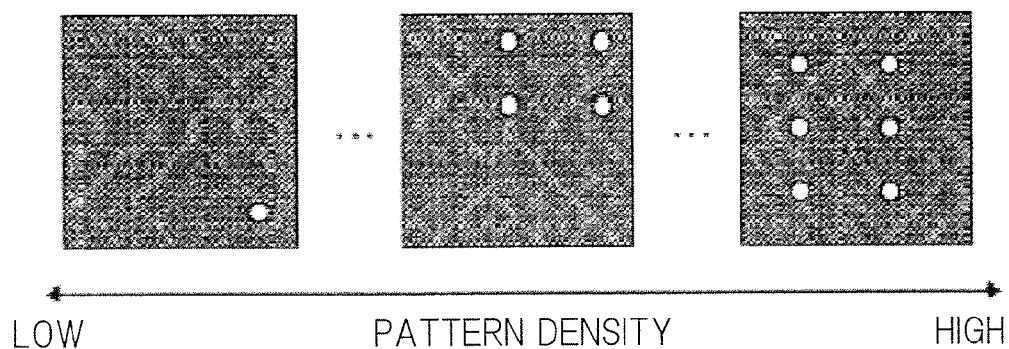
LOW ← PATTERN DENSITY → HIGH
(b) RESULT THAT LAYER 2 IS ARRANGED IN ORDER OF PATTERN DENSITY
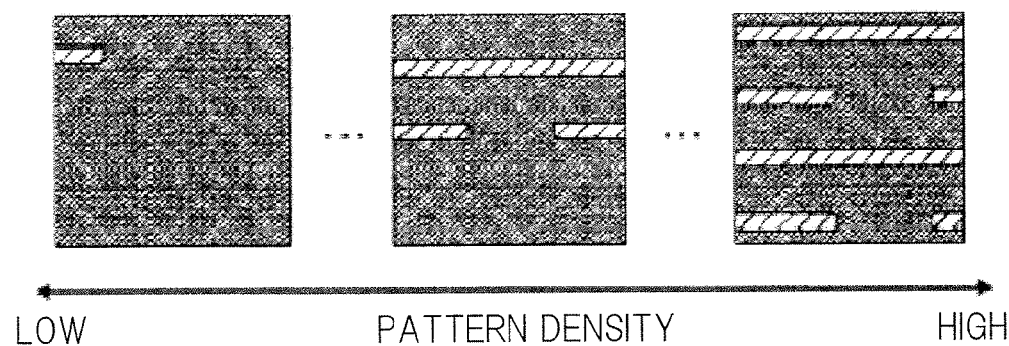
LOW ← PATTERN DENSITY → HIGH

DEFECT ANALYSIS ASSISTANCE DEVICE, PROGRAM EXECUTED BY DEFECT ANALYSIS ASSISTANCE DEVICE, AND DEFECT ANALYSIS SYSTEM

TECHNICAL FIELD

The present invention relates to a defect analysis assistance device of a semiconductor device and a system thereof. In particular, the present invention relates to a technique of using a defect observation image of the semiconductor device and design layout data of the semiconductor device, in a systematic defect analysis of a manufacturing process.

BACKGROUND ART

In the manufacturing process that forms fine patterns on a substrate such as a semiconductor and a liquid crystal, there is a change in a defect to be an analysis target along with the miniaturization of manufacturing patterns. Conventionally, a defect species, which is called as a random defect occurring from dusts and foreign particles, was a target to be analyzed in many cases. However, along with the introduction of an OPC (Optical Proximity Correction) technique, such a case that a systematic defect highly dependent on a layout of a design pattern should be a target to be analyzed has been increasing.

The systematic defect is the defect which occurs caused by specific patterns and layers or a combination of such patterns and layers, the systematic defect can be solved by changing design patterns and layouts, or by changing manufacturing conditions. Therefore, there has been an important problem in improvement of a yield ratio of the semiconductor manufacturing process that the patterns and layers or combinations of such patterns and layers having caused the systematic defect are efficiently specified.

As a technique for efficiently specifying the systematic defect, Patent Document 1 discloses a method in which defect coordinates and design layout data are overlaid (hereinafter, it will be referred to as "matching") to specify patterns and layers in which a defect occurs. Further, Patent Document 2 discloses a technique in which a device pattern is extracted from an image where a semiconductor device is captured, and the extracted pattern and design layout data are overlaid to perform pattern measurements.

PRIOR ART DOCUMENTS

Patent Documents

Patent Document 1: Japanese Patent Application Laid-Open Publication No. 2009-10286
Patent Document 2: Japanese Patent Application Laid-Open Publication No. 2010-28136 (US2007/0023653)

DISCLOSURE OF THE INVENTION

Problems to be Solved by the Invention

In Patent Document 1, although the defect positions and design layout data are overlaid to specify the patterns and layers where the systematic defect occurs, there is no specific disclosure on a selection method for layers to be overlaid, so when the number of layers to be overlaid is large, there is a problem that much time is required for selecting the layers.

Further, in Patent Document 2, as a method for achieving automatic overlay of analysis target images and design layout data with a high precision, disclosed is a method in which patterns are extracted from images to compare the extracted patterns and the design layout data. However, there is no specific disclosure on a selection of layers to be overlaid, so that there is a similar problem as in Patent Document 1. This is because Patent Document 2 is invented, assuming measurement of manufacturing patterns, it is therefore conceivable that the layers to be overlaid are limited in many cases when measurement of the manufacturing patterns is the purpose.

It is an object of the present invention to provide a defect image analysis method capable of specifying patterns and layers where a defect occurs by overlaying defect images to be analysis targets and design layout data, and a defect image analysis system capable of improving efficiency to select the layers from the design layout data.

Means for Solving the Problems

To solve the problems described above, the present invention is characterized in dividing analysis target images for each hierarchy corresponding to a manufacturing process and generating a plurality of layers; calculating a degree of matching between each of the layer division images and each design layer of the design layout data; and specifying a design layer with a highest degree of matching, of the each design layer as a design layer corresponding to the layer division image.

Effects of the Invention

Since the present invention makes it possible to improve the efficiency to select the layers from the design layout data, it is possible to execute an overlay processing of defect observation images and design layout data with a high precision and speed, while efficiently achieving a systematic defect analysis in a semiconductor device manufacturing process.

BRIEF DESCRIPTIONS OF THE DRAWINGS

Figure 2:
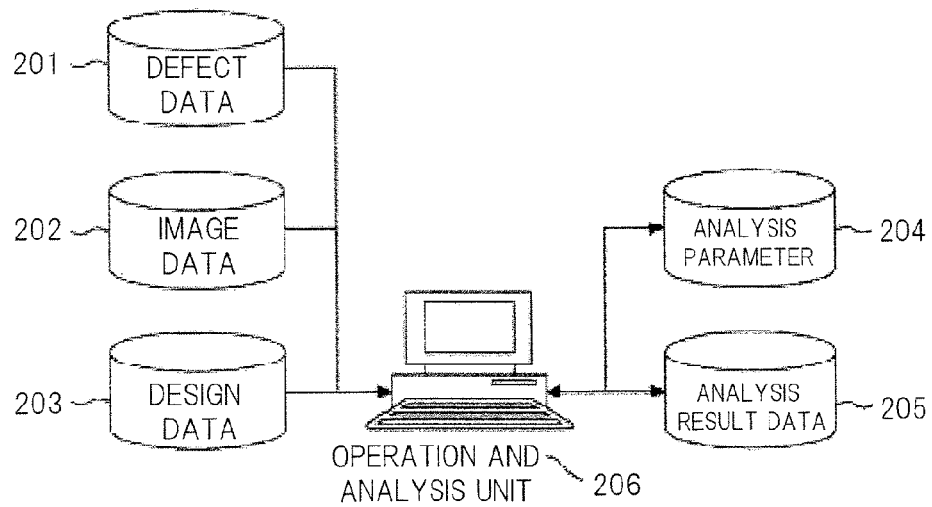
Figure 3:
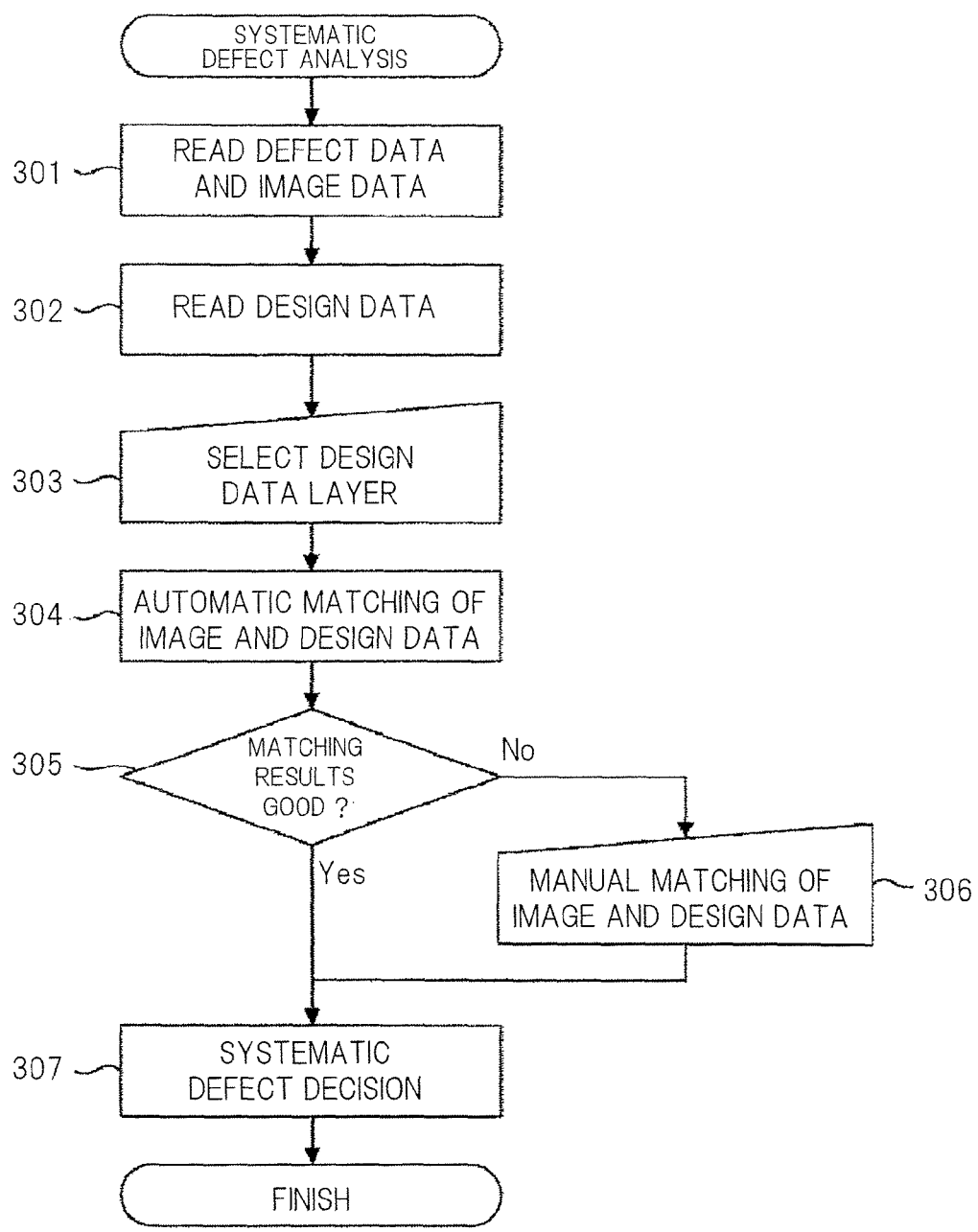
Figure 6:
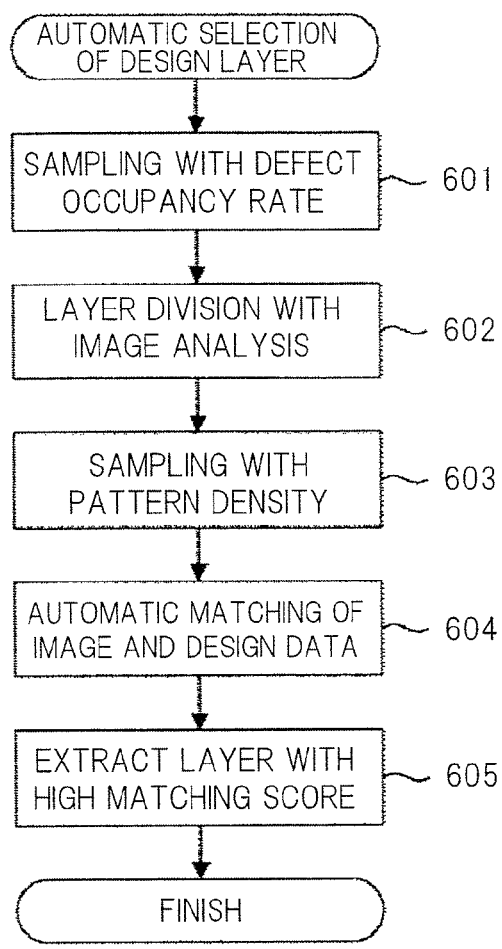
Figure 10:
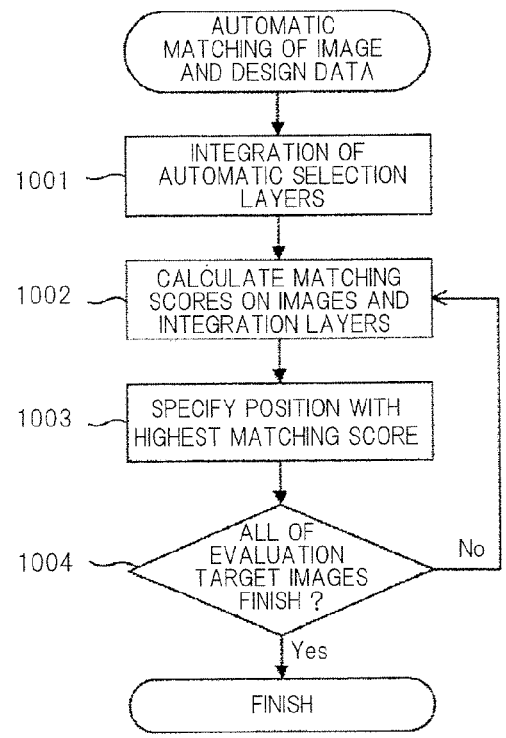
Figure 11:
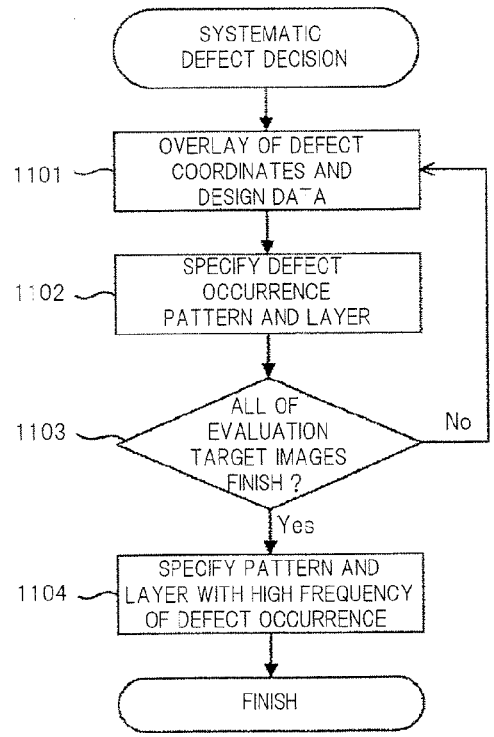
Figure 12:
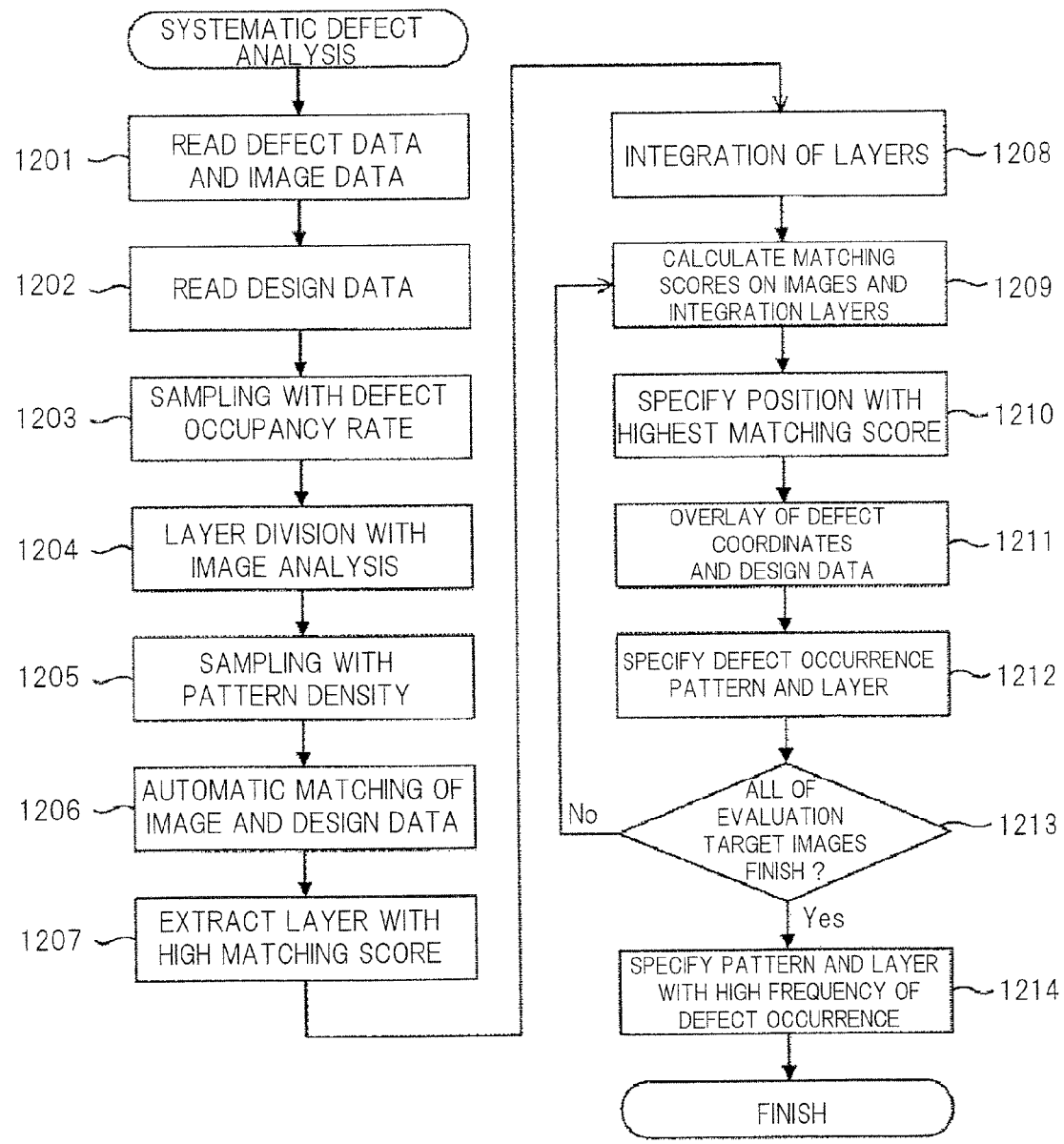

FIG. 1 is a schematic diagram of a SEM defect observation device;
FIG. 2 is a configuration diagram of an operation and analysis unit;
FIG. 3 is a flowchart of a conventional systematic defect analysis processing;
FIG. 4 is a schematic diagram of an overlay processing of a defect observation image and design layout data;
FIG. 5 is a schematic diagram illustrating influence of a defect occupancy rate occupied in the defect observation image;
FIG. 6 is a flowchart of a design layer automatic selection processing;
FIG. 7 is a schematic diagram of a layer division processing using a brightness histogram;
FIG. 8 is a schematic diagram of the layer division processing;
FIG. 9 is a schematic diagram of sampling by pattern density;
FIG. 10 is a flowchart of an automatic matching processing of the defect observation images and the design layout data;
FIG. 11 is a flowchart of the systematic defect decision processing; and FIG. 12 is a flowchart of the systematic defect analysis processing in a present embodiment.

BEST MODE FOR CARRYING OUT THE INVENTION

A configuration example of a SEM defect observation system having functions to execute a systematic defect analysis efficiently will be described. Note that an example in which the systematic defect analysis is executed with a SEM defect observation device as a configuration example of the SEM defect observation system will be described; however, the system configuration is not limited thereto, and some or all of the devices configuring the system may be configured with different devices. For example, the systematic defect analysis processing of the present embodiment may be executed by a defect classifying device connected to the SEM defect observation system through a network, or may be achieved by causing a general-purpose CPU installed in a general-purpose computer in the system to execute a program that executes desired computing processing. The existing devices can be upgraded by a recording medium having the program recorded therein.

Further, the present invention is not only applied to the SEM defect observation system, but can be applied to a defect analysis assistance device connected to an observation device such as a review device, and, of course, can be applied to the defect analysis system.

Hereinafter, the SEM defect observation system is the device for obtaining a high-quality SEM image of observation coordinates, setting defect coordinates detected by upper defect inspection devices such as optical or SEM inspection devices as input information, or setting coordinate information on observation points extracted by simulation, etc. based on the design layout data as input information. Further, a configuration example having systematic analysis functions that specify patterns and layers where a defect readily occurs will be described, setting obtained images and design layout data as input information. In the present embodiment, the systematic defect is the defect occurring in same or similar pattern parts or layers, and the defect highly dependent on a layout of a design pattern.

FIG. 1 is a schematic diagram illustrating an overall configuration of a SEM observation apparatus of the present embodiment. The SEM observation apparatus in FIG. 1 includes an electronic optical system configured with optical elements such as an electronic gun 101, a lens 102, a deflector 103, an objective lens 104, a sample 105 and a secondary particle detector 109, a stage 106 that makes a sample holder for holding a sample to be observed move to an XY surface, an electronic optical system control unit 110 that controls various optical elements included in the electronic optical system, an A/D convertor 111 that quantizes output signals of the secondary particle detector 109, a stage control unit 112 that controls the stage 106, an overall control unit and analysis unit 113, an image processing unit 114, an operation unit 115 having a display, keyboard and mouse, a storage device 116 that retains data such as obtained images, an optical microscope 117, etc. Further, the electronic optical system, the electronic optical system control unit 110, the A/D convertor 111, the stage 106 and the stage control unit 112 compose a scanning electron microscope that is imaging means of the SEM image. Note that the imaging means is not limited to the scanning electron microscope.

A first electronic beam 107 emitted from the electronic gun 101 is focused on the lens 102 and deflected by the deflector 103, and then focused on the objective lens 104, and the sample 105 that is a target to be inspected is irradiated with the first electronic beam 107. From the sample 105 irradiated with the first electronic beam 107, secondary particles 108 such as secondary electrons and reflection electrons are generated, depending on a shape and material of the sample. The generated secondary particles 108 are detected by the secondary particle detector 109 and converted into digital signals by the A/D convertor 111. The output signals of the secondary particle detector 109 converted into the digital signals may be referred to as image signals. The output signals of the A/D convertor 111 are inputted into the image processing unit 114 to generate the SEM image. The image processing unit 114 executes various image processing techniques such as an ADR (Automatic Defect Review) processing that executes an image processing such as defect detections, using the generated SEM image.

The optical elements such as the lens 102, the deflector 103 and objective lens 104 in the electronic optical system are controlled by the electronic optical system control unit 110. The sample is positionally controlled by the stage 106 controlled by the stage control unit 112. The overall control unit 113 is the control unit that controls the overall SEM observation apparatus comprehensively. The overall control unit 113 interprets inputs from the operation unit 115 having a display, keyboard and mouse and the storage device 116, controls the electronic optical system control unit 110, the stage control unit 112 and the image processing unit 114, etc., and outputs the processing results to a display unit included in the operation unit 115 and the storage device 116 if necessary. The processing executed by the image processing unit 114 can be achieved in the form of hardware or software. When the processing is configured with hardware, a plurality of computing elements that execute the processing are integrated on a wiring substrate or in a single semiconductor chip or package. When the processing is configured with software, a high-speed general-purpose CPU is installed in the image processing unit 114, and a program that executes a desired computing processing is executed.

FIG. 2 illustrates the details of the overall control unit and analysis unit 113 of FIG. 1. An operation and analysis unit 206 illustrated in FIG. 2 is expressed by integrating the overall control unit and analysis unit 113 and the operation unit 115 of FIG. 1. The operation and analysis unit 206 responds to operational instructions from the operational unit 115 and is achieved by a plurality of functional blocks achieved by executing a predetermined program incorporated in the overall control and analysis unit 113 by a CPU. In this way, the configuration incorporated in the SEM observation apparatus illustrated in FIG. 1 is possible, but the operation and analysis unit illustrated in FIG. 2 may be configured independently from the SEM observation apparatus illustrated in FIG. 1, and the configurations in FIG. 1 and FIG. 2 may be connected to each other through a network. When the configuration is incorporated in the SEM observation apparatus illustrated in FIG. 1, a defect data storage unit 201, an image data storage unit 202, a design layout data storage unit 203, an analysis parameter storage unit 204 and an analysis result data storage unit 205 may be common with the storage device 116. The defect data storage unit 201 stores defect data that stores information such as defect coordinates. The image data storage unit 202 stores image data storing defect images captured by the SEM observation apparatus. The design layout data storage unit 203 stores design layout data that stores design information such as design layout information. The analysis parameter storage unit 204 stores analysis parameters that store analysis conditions of such as image processing, which is executed on defect images upon analysis.

The operation and analysis unit 206 overlays defect images and design layout data by setting defect data, image data, the design layout data and analysis parameters as inputs. Then, the operation and analysis unit 206 specifies design patterns or layers where a defect occurs to perform a decision processing as a systematic defect. Note that the operation and analysis unit 206 in the present embodiment includes a layer division unit that divides the captured defect images for each hierarchy corresponding to a manufacturing process and generates a plurality of layer division images, a matching processing unit that calculates a degree of matching between each of the layer division images and each design layer of the design layout data, a design layer specifying section that specifies a design layer with a highest degree of matching of each design layer as a design layer corresponding to the layer division image, a first sampling unit that samples defect images to be analysis targets, and a second sampling unit. Processing details of the layer division unit, the matching processing unit, the design layer specifying section, the first sampling unit and the second sampling unit will be described later. The processing results are stored into the analysis result data storage unit 205. Further, when the analysis parameters are adjusted upon analysis, the adjustment results may be stored into the analysis parameter storage unit 204 to make use of the results in the next analysis.

FIG. 3 is a flowchart of the conventional systematic defect analysis process. First, defect data and image data are read (301). Further, design layout data is read (302). The processing of the step 301 and step 302 may be performed in parallel or in reverse.

Next, a layer to be overlaid with a defect image is selected from the design layout data (303). Conventionally, a user selected an optimum layer by comparing images with design patterns. Since the layers of the design patterns were more than one hundred in some cases, much time was required for selecting the layers when the number of layers to be overlaid was large. Therefore, it is preferable to refine the number of layers at minimum because the processing time is increased in proportion to the number of layers to be overlaid.

As to process names of captured observation images and layer names of the design layout data, when their relationship is managed by naming rules that are easily guessed, a layer can be selected relatively easily; however, a department for naming the process names of the captured observation images, a department for deciding the layer names of the design layout data and a department for analyzing systematic defects are different in many cases, so that the operation for refining the layers to be overlaid by using the design layout data is dependent on experience and knowledge of a person in charge in each department. Therefore, the operation was a burden for especially beginners.

Next, the image and design layout data are subjected to automatic matching (304). Specifically, setting pattern information extracted from the image as a template, a position with a highest degree of matching on the design layout data is calculated as matching coordinates. For example, a defect observation image is illustrated in FIG. 4(*a*), and it is set as a template. (401) indicates a defect region. As illustrated in FIG. 4(*b*), the design layout data that is a matching target is set as a matching target area with a larger region than the defect observation image in an observation field of view (FOV). This is because the defect position information includes errors caused by stage accuracy of the inspection device or the SEM observation apparatus. FIG. 4(*c*) shows that a part with a highest degree of matching is overlaid as a matching position (for example, 402) after searching a region of the design layout data (b) with the defect observation image (a) as a template. In this manner, the position where a defect occurs can be specified on design layout data.

Due to stage accuracy of the inspection device, etc., a defect position specified by the defect inspection device may include micron-order errors, so when the defect occurring in the pattern with a nano-order size is analyzed, the defect is not precisely analyzed in some cases due to such errors. In this case, conventionally, the defect position and design layout data were overlaid by manual, that is, by manual assistant operation. However, there has been a problem in terms of operation efficiency.

Further, there is also a problem that matching accuracy is deteriorated depending on the defect images. As in the case of FIG. 4 and FIG. 5(*a*), when a defect region is not large with respect to the FOV (for example, 501), it can be solved by the matching processing disclosed in Patent Document 2. However, since an object of Patent Document 2 is to perform pattern measurements, as illustrated in FIG. 5(*b*), the case in which the defect region is large with respect to an observation image in the FOV (for example, 502) is not assumed. In the case of setting the defect image obtained by the SEM observation apparatus as an analysis target, not only the manufacturing pattern is included in the analysis target image, but the defect image is also included in analysis target image; therefore, the image and design layout data are not successfully overlaid in some cases, particularly when a defect size is very large with respect to the FOV (Field Of View). In this case, the matching accuracy is deteriorated and modified operation of overlaying results by manual assistance is required; therefore, there has been a problem that burden of the operation in the systematic defect analysis cannot be minimized.

When a matching accuracy of the image and design layout data is not reliable, checking of matching results is required by visual observation (305). When the matching results are good, the step goes to a systematic defect decision (307), but when the matching results are not good, the step goes to the systematic defect decision processing (307) after the matching processing is performed by manual (306). Such checking of the matching results and modification of the same by manual are burdens of operators, thereby requiring improvements of the matching accuracy.

When the image and design layout data are completely overlaid, the systematic defect decision processing is performed (307). Specifically, the defect information is further overlaid on where the image and design layout data are overlaid to specify the design layout data or the layer where a defect occurs. As described above, although Patent Document 1 discloses a method of performing statistical processing after specifying a defect position and specifying the layer where the defect readily occurs, much time is required for specifying a defect position on design layout data, and operation burden by manual operation is also a problem, it is therefore difficult to say that the method is widely put into practical use. According to the present embodiments described below, since such problems are solved, it is possible to minimize the burden of operation in the systematic defect analysis.

FIG. 6 is a flowchart achieving automatic processing of design layer selection (303) of FIG. 3.

First, a first sampling with a defect occupancy rate is performed (601). Hereinafter, the sampling is to select and extract an image to be used as an analysis target from a plurality of images. This is performed by a first sampling unit in the operation and analysis unit 206. At this time, since the size of a defect area occupied in a defect image in the FOV is more important, as a criterion for decision, than an actual size of the defect, the defect occupancy rate is defined by Equation (1) as a sampling criterion. In Equation (1), the defect occupancy rate is set as P, a defect area is set as $S_{Defect}$, and the FOV is set as $S_{FOV}$.

[Expression 1]

$$P = \frac{S_{Defect}}{S_{FOV}} \qquad \text{Equation (1)}$$

As output information of the inspection device, the defect area stored in the defect information may be used, but when the ADR is executed in the SEM observation apparatus upon obtaining the defect image, since more accurate defect position and size are detected, it is preferable to use such a position and size. Setting the defect occupancy rate defined by Equation (1) as a criterion, a defect with a low defect occupancy rate is sampled. However, if no defect exists, it is not subjected to the systematic defect decision. As illustrated in FIG. 5(a), since the pattern hidden and lost in the defect is few with a low defect occupancy rate, matching accuracy with respect to the design layout data is improved. Further, with the low defect occupancy rate, since the possibility in which matching scores are calculated by mistaking an edge of the defect part as an edge of the manufacturing pattern is decreased, it is possible to improve the matching accuracy with respect to the design layout data. The equations of the matching score calculation will be described later, with reference to Equations (2) and (3).

Next, a layer division with image analysis is performed on an image sampled with a defect occupancy rate (602). A layer division processing in step 602 is to divide the image for each hierarchy corresponding to a manufacturing process and to generate a plurality of layer division images. This is performed by a layer division unit in the operation and analysis unit 206. As an example of the layer division method, the layer division may be performed by an edge detection disclosed in Patent Document 2, or as illustrated in FIG. 7, the layer division may be performed depending on the number of layers by estimating the number of layers from brightness distribution histogram of the SEM image to be an analysis target. Herein, a layer is a hierarchy that corresponds to a manufacturing process.

FIG. 7 illustrates a case that the number of layers is one (a), a case that the number of layers is two (b), and a case that the number of layers is three (c). Note that the number of layers indicates the number of layers formed on a substrate (darkest part in each of FIG. 7(a), FIG. 7(b) and FIG. 7(c)). Although the number of layers can be automatically calculated from the brightness distribution histogram of the SEM image, when the number of layers appeared in the SEM image is known, or when it is preferable to specify the number of layers in more certain way, an operator may input the number of layers, using the operation unit 115 of FIG. 1 or a layer division unit in the operation and analysis unit 206 of FIG. 2.

FIG. 8 illustrates a schematic diagram of an observation image (a) before the layer division processing (602). FIG. 8 also illustrates schematic diagrams of a layer 1 (b1) extracted by layer division, a layer 2 (b2) extracted by layer division and a layer 3 (b3) extracted by layer division, which are layer division images after the layer division by the method described in FIG. 7 or depending on the number of layers input by an operator. Further, the design layers (c1) to (c3) that respectively correspond to (b1) to (b3) are illustrated. The design layers (c1) to (c3) are stored into a design database. As described later, in step 605, the design layout data corresponding to each of the division images (b1) to (b3) is extracted, while the layers (c1) to (c3) become target layers at this point.

When the pattern extraction for each layer is completed by the layer division (602) with image analysis, a second sampling is performed, setting the extracted pattern density as a criterion (603). This is performed by a second sampling unit in the operation and analysis unit 206. In order to perform matching of the image and design layout data precisely, since it is preferable that more patterns are appeared in the FOV, an image with a high pattern density is sampled. The pattern density can be defined by an occupancy rate of the pattern part in the FOV, or by sum of lengths of pattern edges. As to what definition is to be adopted, optimum algorism is adopted in accordance with matching algorism of the observation images and design layout data. In the example of FIG. 9, the observation images are arranged such that they have a higher pattern density from left to right. The right side image with a higher pattern density is preferentially set as an evaluation target. However, when there is a huge difference in the pattern density of each layer, only the image in which a specific layer with a high density is appeared is sampled in some cases as a result of sampling based on the pattern density, it is therefore required to take some measures. As the specific measures, the pattern density is calculated for each layer to sample the image with a high pattern density for each layer as illustrated in FIG. 9, thereby being able to prevent the sampling results from being concentrated on the observation image in which the specific layer is appeared.

After the matching processing targets are refined by sampling that sets a defect occupancy rate for the observation image in the FOV as a criterion and further by sampling that sets the pattern density appearing in the observation image as a criterion, the matching processing of the image and design layout data is performed (604). In step 604, the matching process is to calculate a degree of matching between each of the layer division images and each design layer of the design layout data. This is performed by the matching processing unit in the operation and analysis unit 206. In step 604, a matching score is calculated for each layer that is extracted by a layer division with image analysis. The matching score is a calculation equation that is defined so as to make a degree of matching between the layer division image and the design layout data higher. The calculation equation for a general correlation coefficient is shown in Equation (2) as an example. Herein, a correlation coefficient is set as $\rho_{ijk}$, a layer division image is set as M, and design layout data is set as I, an average of pixel values of the layer division image M is set as $\overline{M}$, and an average of pixel values of the design layout data I is set as $\overline{I}$. Note that p expresses each pixel included in the image and q expresses the total number of pixels included in the image.

[Expression 2]

$$\rho_{ijk} = \frac{\sum_{p=1}^{q}(M_p - \overline{M})(I_p - \overline{I})}{\sqrt{\sum_{p=1}^{q}(M_p - \overline{M})^2}\sqrt{\sum_{p=1}^{q}(I_p - \overline{I})^2}}$$

Equation (2)

The layer division is performed on each image, and the matching scores are calculated, using a calculation equation that is defined so as to increase the scores according to a degree of matching between the image and design layout data as in Equation (2). $\rho_{ijk}$ in Equation (2) expresses correlation values between a j-th layer division image included in an i-th image and a k-th design layer. Note that when x images are left as result evaluation targets sampled in steps 601 and 603, it is $1 \leq i \leq x$, and when the number of layers divided in step 602 is y, it is $1 \leq j \leq y$, and when the number of design layers as a matching target is z, it is $1 \leq k \leq z$.

The matching scores are calculated, the scores between each of the layer division images (b1 to b3 in FIG. 8) extracted from each image and each of the design layers of matching targets (a plurality of design layers including c1 to c3 in FIG. 8). That is, $\rho_{ijk}$ is calculated with respect to each pair of (i, j, k). Herein, the layers of matching targets may be all layers of the design layout data, or a plurality of layers which are preliminarily selected by a user. By setting all design layers as a matching target, an optimum design layer can be extracted without depending on how a user selects the layer. Further, when a user selects a plurality of design layers as matching targets, higher certainty is obtained by largely selecting matching targets. On the other hand, a minimum layer selection is required in terms of calculation costs. For example, when a correspondence between manufacturing step names and design layer names is understandable, a layer to be a matching target can be effectively selected by selecting a plurality of front-back layers including the design layers corresponding to the manufacturing layer names.

Next, as in Equation (3), a calculation equation capable of deciding a design layer with a high degree of matching is defined with respect to each layer division image extracted from the images, thereby extracting the design layer with the high degree of matching with respect to each layer extracted from the images (605). This is performed by the design layer specifying section in the operation and analysis unit 206. Here, $F_{jk}$ in Equation (3) expresses an average of correlation values of the k-th design layer with respect to the j-th layer division image that is extracted from each image (i=1 to n) over n images, which uses the average as a matching score. In Equation (3), a simple average is defined as a matching score, but a coefficient that reflects the pattern density, etc. may be introduced in Equation (3).

[Expression 3]

$$F_{jk} = \frac{1}{X}\sum_{i=1}^{x}\rho_{ijk}$$

Equation (3)

In this way, the matching scores between each layer division image extracted from the images and each design layer are calculated, thereby extracting the design layer with the highest matching score with respect to each later division image extracted from the images. That is, z matching scores of $F_{j1} \ldots F_{jk} \ldots F_{jz}$ are calculated, and when $F_{jkmax}$ is the greatest score among the matching scores, a $k_{max}$-th design layer is specified as a layer corresponding to the j-th layer division image. This is repeated until j= from 1 to z by "z" which is the number of layers of the layer division images, thereby specifying the design layer with a highest matching of degree with respect to all layer division images.

The above-described processing makes it possible to automatically extract a design layer to be evaluated which is overlaid on an image. Therefore, the design layer to be evaluated, which is overlaid on the image, is automatically selected, irrespective of the operator's knowledge and experience. Further, since the design layer is selected according to a captured image, even when the same layer is viewed differently depending on the layer in which the image is captured, an optimum design layer can be extracted.

Further, in the present embodiment, the example in which the observation images used for matching with the design data are preliminarily sampled is described in steps 601 and 603, but the processing in steps 602, 604 and 605 may be performed on each of the observation images to extract a layer with a high matching score. However, as described above, it is preferable that optimum images to be used for the layer extraction are sampled before being matched with design data in term of calculation costs. In the present embodiment, since the matching target images are limited to the minimum by sampling with a defect occupancy rate, or by sampling with pattern density, the processing time is minimized.

FIG. 10 is a flowchart explaining the processing that the positioning of images and design layout data is automatically performed with a high precision. This processing corresponds to step 304 in the conventional flowchart of FIG. 3. Conventionally, as described in FIG. 3, after the image and design layout data were automatically matched (304), whether the matching results are checked by visual observation (305), the modification of the matching results is required with respect to the image by manual (306) when the matching results were not good. The matching accuracy is deteriorated when a defect occupancy rate occurring in the image to be matched is high while pattern information to be matched is small, or when a defect is mistaken as a pattern, or when a design layer to be a matching target is inappropriately selected. According to the present embodiment, since the observation image of which the occupancy rate is too high can be excluded from the matching target by sampling (601) that sets the occupancy rate described in FIG. 6 as a criterion, and further since the design layer with a high degree of matching with respect to the image is extracted (605), the design layer as a matching target is not inappropriately selected, it is possible to prevent the matching accuracy from being deteriorated.

Further, if the positioning is performed by matching each of the divided layers and the defect images, when there is a periodic pattern, the matching may be performed at a position shifted by an integer multiple of the period. Therefore, in the present embodiment, since the defect images are matched with the integrated layers, it is possible to improve the matching accuracy even when a periodic pattern exists in one layer.

A specific flowchart of FIG. 10 will be described. First, as front-end processing for executing auto matching processing, the layers of which the extracted matching scores are high (605) are integrated as described in FIG. 6, and set as design layout data that is a matching target (1001).

Next, the matching (positioning) between the integrated design layout data and the defect images is performed to calculate the matching scores (1002), and the position with a highest matching score is specified as an overlay position of the images and design layout data (1003). The processing for confirming the overlay position is executed on all of the evaluation target images (1004).

FIG. 11 is a flowchart explaining the processing to perform a systematic defect decision with a high precision. This processing corresponds to step 307 in the conventional flowchart of FIG. 3. First, the defect coordinates are overlaid on the same position as an overlay position of the images and design layout data that is extracted in FIG. 10 (1101). This enables the defect coordinates and design layout data to be overlaid at an optimum position, thereby being able to precisely specify the pattern and layer where a defect occurs (1102). The processing for specifying the defect occurrence patterns and layers is executed on all of the evaluation target images (1103). The defect occurrence patterns and layers are specified to all of the evaluation target images, and the defect which highly frequently occurs in the same pattern or layer is extracted to decide such a defect as a systematic defect (1104). Since this enables the pattern or layer where the defect occurs to be understandable, a user can reduce an occurrence of the defect by reviewing the pattern, a design layout of the layer, and the manufacturing process.

FIG. 12 is a flowchart of a systematic defect decision incorporating modification processing of the present embodiment into the flowchart in the conventional systematic defect decision of FIG. 3. Firstly, defect data and image data are read (1201). This processing corresponds to (301) in FIG. 3, and in the case of the storage device 116 in the SEM observation apparatus of FIG. 1 or in the case of the analysis system that is connected to the SEM observation apparatus through a network, the data is read from the defect data storage unit 201 and the image data storage unit 202 of FIG. 2.

Next, the design layout data is read (1202). This processing corresponds to (302) in FIG. 3, and in the case of the storage device 116 in the SEM observation apparatus or the analysis system that is connected to the SEM observation apparatus through a network, the data is read from the design layout data storage unit 203 of FIG. 2. With analysis of the read defect data and image data, the image with a low occupancy rate is sampled (1203). This processing corresponds to (601) in FIG. 6.

Next, by targeting the images with a low occupancy rate extracted by sampling, a layer division is performed by the image analysis (1204). This processing corresponds to (602) in FIG. 6. The sampling is performed by pattern density based on the results of the layer division (1205), and the images to be analysis targets for layer extraction and target images of the design layout data matching processing are further refined. This processing corresponds to (603) in FIG. 6.

Further, by targeting the images refined by sampling, the matching processing is performed on the design layout data with respect to each layer extracted from the images (1206). This processing corresponds to (604) in FIG. 6. The matching scores are calculated with respect to each layer extracted from the images, and the design layer with a high matching score is extracted, as an evaluation target layer, with respect to each layer division image extracted from the images (1207). This processing corresponds to (605) in FIG. 6.

Next, the step goes to a processing flow in which the automatic matching processing (304) of the image and design layout data in FIG. 3 is improved. First, the design layers extracted as an evaluation target are integrated to generate the design layout data as a target to be overlaid on the image (1208). This processing corresponds to (1001) in FIG. 10.

Next, in order to precisely analyze a positional relationship between a defect occurrence pattern and design pattern, the matching processing between the integrated layout data and evaluation target images is performed (1209). This processing corresponds to (1002) in FIG. 10.

The position with the highest matching score is specified as an overlay position of the image and design layout data (1210). This processing corresponds to (1003) in FIG. 10.

The defect coordinates are further overlaid on the overlay position calculated in (1210) (1211). This processing corresponds to (1101) in FIG. 11. This enables the defect coordinates and design layout data to be overlaid precisely, thereby being able to precisely specify the pattern and the layer where a defect occurs (1212). This processing corresponds to (1102) in FIG. 11.

The processing is performed on all of the images to be analysis targets (1213), the defect with a high frequency occurring in the same pattern or layer is extracted to decide such a defect as a systematic defect, thereby specifying the pattern or layer where the systematic defect occurs (1214). This processing corresponds to (1104) in FIG. 11.

Further, the present invention is not limited to the above-described embodiments and various modification examples are contained. For example, the above-described embodiments have been described in detail for easy understanding of the present invention and are not necessarily limited to inclusion of all the configurations described. Moreover, part of the configuration of an embodiment may be replaced by the configuration of another embodiment, and further the configuration of an embodiment may be added to the configuration of another embodiment. Further, part of the configuration of the embodiments may be subjected to addition, deletion and replacement of other configuration.

DESCRIPTION OF REFERENCES

101 electronic gun
102 lens
103 deflector
104 objective lens
105 sample
106 stage
107 first electronic beam
108 secondary particle
109 secondary particle detector
110 electronic optical system control unit
111 A/D convertor
112 stage control unit
113 overall control unit and analysis unit
114 image processing unit
115 operation unit
116 storage device
117 optical microscope
201 defect data storage unit
202 image data storage unit
203 design layout data storage unit
204 analysis parameter storage unit
205 analysis result data storage unit
206 operation and analysis unit
401 defect region

The invention claimed is:

1. A defect analysis assistance device comprising:
a processor; and
memory storing one or more programs for execution by the processor, the one or more programs including instructions for:
analyzing a defect of a target to be inspected;
dividing analysis target images among observation images of sample patterns of the target to be inspected with respect to each of a plurality of layers according to a manufacturing process by an image analysis or an operator's specification;
generating a plurality of layer division images;
calculating a degree of matching between each of the layer division images and each design layer of the design layout data; and
specifying a design layer with a highest degree of matching of the each design layer as a design layer corresponding to the layer division image,
wherein analysis target images are sampled from the observation images based on an occurrence rate of a manufacturing pattern for each hierarchy occupied in the images to be observed.

2. The defect analysis assistance device according to claim 1, wherein the analysis target images are sampled from the observation images based on an occupancy rate of a defect occurrence region occupied in the observation images.

3. The defect analysis assistance device according to claim 1, wherein a positioning processing is performed by integrating a plurality of design layers specified as a design layer corresponding to each of the layer division images, and overlaying the integrated design layout data and the analysis target images.

4. The defect analysis assistance device according to claim 1, wherein the design layers of the design layout data are set as a processing target for calculating the degree of matching.

5. A non-transitory computer readable media configured to store a program to be executed in a defect analysis assistance device, the program comprising instructions for:
analyzing a defect of a target to be inspected;
dividing analysis target images among observation images of sample patterns of the target to be inspected with respect to each of a plurality of layers according to a manufacturing process by an image analysis or an operator's specification;
generating a plurality of layer division images;
calculating a degree of matching between each of the layer division images and each design layer of the design layout data; and
specifying a design layer with a highest degree of matching of the each design layer as a design layer corresponding to the layer division image,
wherein analysis target images are sampled from the observation images based on an occurrence rate of a manufacturing pattern for each hierarchy occupied in the images to be observed.

6. The non-transitory computer readable media configured to store the program according to claim 5, wherein the analysis target images are sampled from the observation images based on an occupancy rate of a defect occurrence region occupied in the observation images.

7. The non-transitory computer readable media configured to store the program according to claim 5, wherein a positioning processing is performed by integrating a plurality of design layers specified as a design layer corresponding to each of the layer division images, and overlaying the integrated design layout data and the analysis target images.

8. The non-transitory computer readable media configured to store the program according to claim 5, wherein design layers of the design layout data are set as a processing target for calculating the degree of matching.

9. A defect analysis system including:
an electron microscope that irradiates a target to be inspected with charged particle radiation, and stores observation images with sample patterns of the target to be inspected by detecting secondary particles from the target to be inspected; and
a computer that analyzes a defect of the target to be inspected, the defect analysis system executing instructions for:
dividing analysis target images among observation images of sample patterns of the target to be inspected with respect to each of a plurality of layers according to a manufacturing process by an image analysis or an operator's specification;
generating a plurality of layer division images;
calculating a degree of matching between each of the layer division images and each design layer of the design layout data; and
specifying a design layer with a highest degree of matching of the each design layer as a design layer corresponding to the layer division image,
wherein analysis target images are sampled from the observation images based on an occurrence rate of a manufacturing pattern for each hierarchy occupied in the images to be observed.

10. The defect analysis system according to claim 9, wherein the analysis target images are sampled from the observation images based on an occupancy rate of a defect occurrence region occupied in the observation images.

11. The defect analysis system according to claim 9, wherein a positioning processing is performed by integrating a plurality of design layers specified as a design layer corresponding to each of the layer division images, and overlaying the integrated design layout data and the analysis target images.

12. The defect analysis system according to claim 9, wherein design layers of the design layout data are set as a processing target for calculating the degree of matching.

* * * * *